Figure 1:
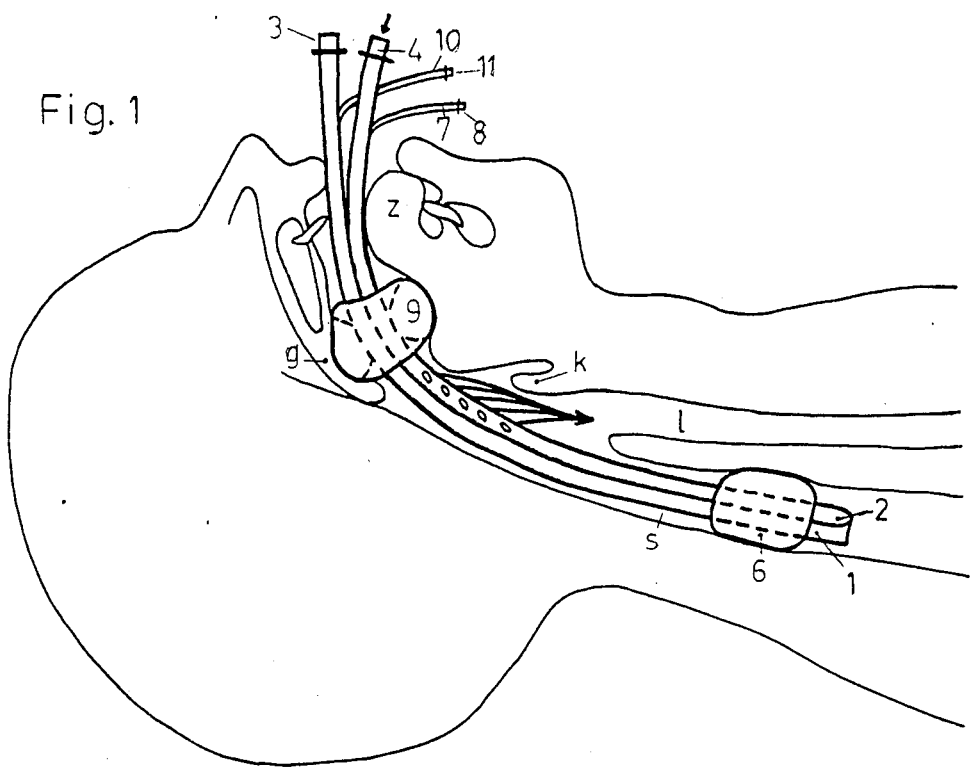

United States Patent [19]

Frass et al.

[11] Patent Number: 4,688,568
[45] Date of Patent: Aug. 25, 1987

[54] RESPIRATORY TUBE OR AIRWAY

[76] Inventors: Michael Frass, Viechtlgasse 11;
Reinhard Frenzer,
Johann-Strauss-Gasse 24, both of
Mödling, Austria, A-2340; **Jonas
Zahler**, Walfischgasse 5, Wien,
Austria, A-1010

[21] Appl. No.: 828,780

[22] Filed: Feb. 11, 1986

[30] Foreign Application Priority Data

Feb. 20, 1985 [AT] Austria .................................. 513/85

[51] Int. Cl.⁴ ............................................ A61M 16/00
[52] U.S. Cl. ............................. 128/207.15; 604/275;
128/202.28
[58] Field of Search ....................... 128/207.15, 207.14,
128/200.26, 202.28, 203.11; 604/275, 282

[56] References Cited

U.S. PATENT DOCUMENTS

| | | | |
|---|---|---|---|
| 3,630,207 | 12/1971 | Kahn et al. | 604/282 |
| 3,683,908 | 8/1972 | Michael et al. | 128/145 |
| 3,841,319 | 10/1974 | Michael et al. | 128/28 |
| 4,090,518 | 5/1978 | Elam | 128/349 B |
| 4,091,816 | 5/1978 | Elam | 128/207.15 |
| 4,155,365 | 5/1979 | Boslau | 128/351 |
| 4,230,108 | 10/1980 | Young | 128/207.15 |
| 4,327,721 | 5/1982 | Goldin et al. | 128/207.15 |
| 4,351,330 | 9/1982 | Scarberry | 128/207.15 |
| 4,449,526 | 5/1984 | Elam | 128/207.14 |

FOREIGN PATENT DOCUMENTS

| | | |
|---|---|---|
| 376128 | 10/1984 | Austria . |
| 0092618A1 | 4/1982 | European Pat. Off. . |
| 2120164 | 11/1972 | Fed. Rep. of Germany . |
| 2080690A | 2/1982 | United Kingdom . |
| 2086229A | 5/1982 | United Kingdom . |

OTHER PUBLICATIONS

"Mouth-to-Lung Airway" for Cardiac Resuscitation, Methods and Devices section of The Lancet, Dec. 21, 1968 issue, p. 1329.

Primary Examiner—Henry J. Recla
Attorney, Agent, or Firm—Thomas R. Vigil

[57] ABSTRACT

This airway for sole esophageal obturator or endotracheal and esophageal-obturator ventilation by choice has an inflatable cuff in the area of the tip of the airway and air-outlets in its wall in the area of the pharynx.

To enable the use of the airway in emergency-cases reliably and also to enable the insertion by first-aid-personnel only, the airway has an inflatable pharyngeal cuff known per se and surrounding the wall of the airway above the air-outlets in that area, which, when the airway is inserted, is situated between the soft palate and the boundary between the base of the tongue and the back of the tongue.

9 Claims, 7 Drawing Figures

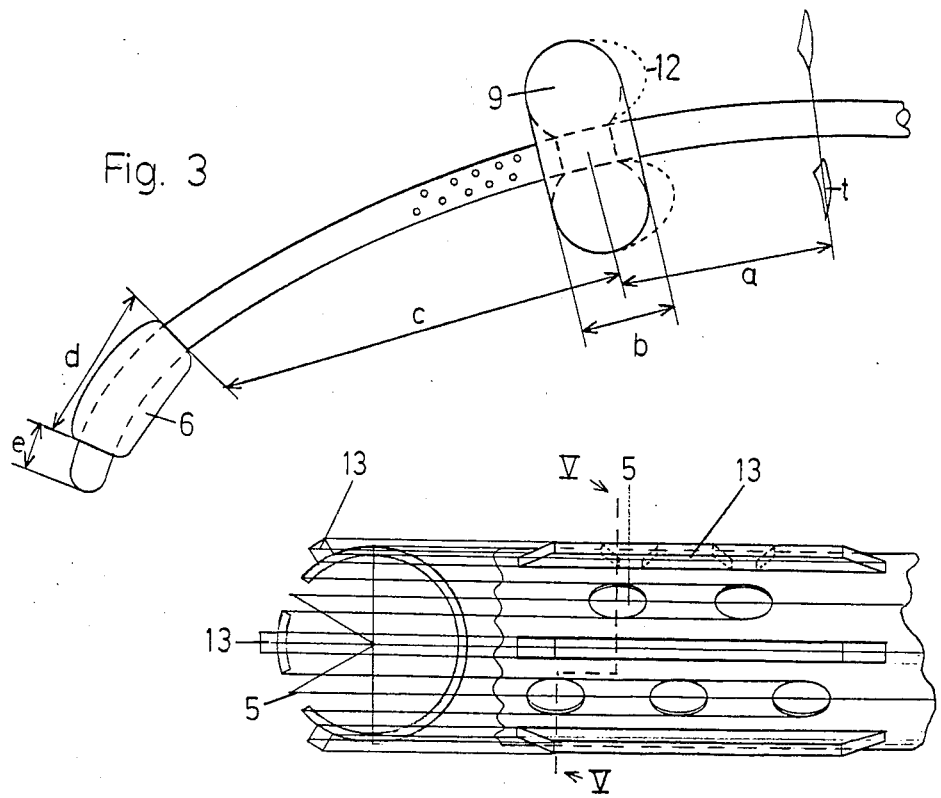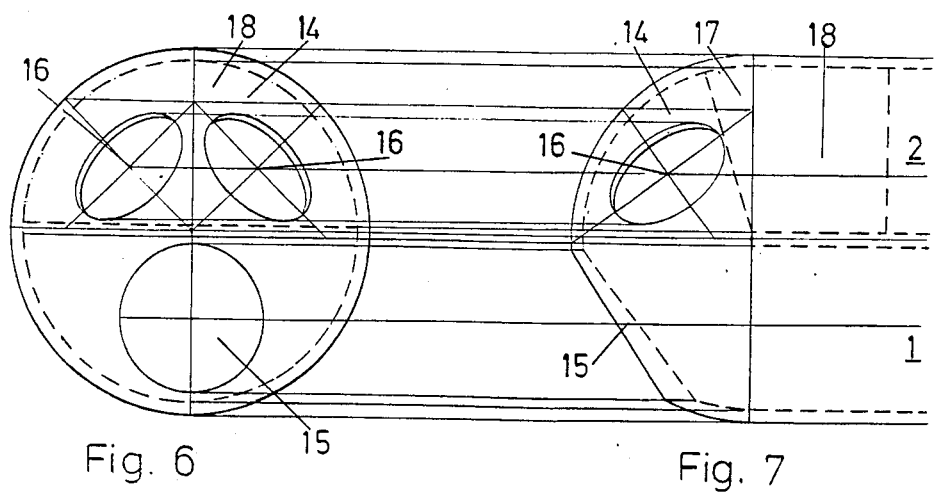

RESPIRATORY TUBE OR AIRWAY

The invention refers to an airway for sole esophageal or endotracheal or esophageal-obturator ventilation by choice, with an inflatable cuff in the area of the tip of the airway and with air-outlets in the wall of the airway in the area of the pharynx.

Airways of this kind have been developed for use in emergency resuscitation, so that the insertion of the airway by first-aid personal should be possible.

A single-lumen airway for insertion into the esophagus and being sealed to the outside by a face mask is known, e.g. by Don Michael T. A., Lambert E. H., Mehran A.: Lancet p. 1329, 1968. During ventilation air is guided from the lumen of the airway through the air-outlets to the patient. However the sealing of the airway against the surrounding air is problematic as one has to press the face mask to the patients face adequately usually demanding an assistant.

A twin-lumen airway of this kind is known from AT-PS No. 376.128. This airway can be inserted into the trachea or into the esophagus by choice. In the first case the air passes from the one lumen directly into the trachea, in the second case the air passes from the other lumen through the air outlets. Also with this airway a face mask is recommended.

According to DE-OS No. 21 20 164 an airway is provided which shows two parallel tubes. The one tube is inserted into the esophagus and may be sealed by a cuff. This tube does not conduct air but is used to withdraw gastric fluid by suction. Ventilation is carried out through the second tube which ends in the cavum pharyngis. For sealing a further cuff may be provided which instead of a mask seals the cavum pharyngis directly. However this airway must not be inserted into the trachea, or esophagus by choice. If this airway is inserted into the trachea, ventilation is impossible. With respect to the drawing moreover it has to be doubted, if the device, as stated in the last paragraph of the description, in fact can be used reliably without medical knowledge and experience.

It is an object of the invention to provide an airway, which can be used reliably, especially in emergency-resuscitation. It should be possible that the insertion may be carried out by first-aid-personnel and that all manipulations may be carried out by only one person as far as possible.

This intention can be fulfilled with an airway as mentioned above which, according to the invention, has an inflatable pharyngeal cuff, known per se and surrounding the wall of the airway above the air-outlets in that area which, when inserted, is situated between the soft palate and the boundary between the base of the tongue and the back of the tongue.

Because of this position of the pharyngeal cuff the soft palate is pushed in a dorsocranial direction when inflating the cuff so that the connection between the cavum pharyngis, the cavum oris and the cavum nasi will be blocked. The remaining dead-volume for already consumed air is very small.

It is advisable if the pharyngeal cuff shows the shape of a torus in general when it is inflated.

A pharyngeal cuff which fits good to the anatomic conditions has a filling-volume of 60 to 110 ml.

Experiments have shown that it is advantageous to place the pharyngeal cuff in a position 9 to 12 cm from that part of the airway which is located between the teeth of the patient when the airway is inserted.

To avoid inadvertent occlusion of the epiglottis it is recommended to make the oral (upper) wall of the pharyngeal cuff thinner than the caudal (lower) wall, so that the cuff expands into the direction of the mouth when being filled to a higher extent.

If the wall of the airway has protuberant bars, naps or the like in the area of the air-outlets, preferably orientated in the longitudinal direction of the airway, it can be avoided that e.g. mucosa is pressed against the holes, resulting in the unwanted effect of a one-way valve.

Especially with twin-lumen airways it is recommended to close the tip with an hollow approximately hemispheric cap which has a hole whose axis is approximately parallel to the axis of the airway and whose diameter is smaller than the diameter of the respective lumen. So it is avoided that particles which pass through the hole can block the lumen of the airway.

It is a further improvement in this regard if the cap has additional holes, their diameter being likewise smaller than the diameter of the open lumen.

For an airway with two parallel lumens there is a simple construction if the cap has a plug which blocks the end of one lumen.

Figure 2:
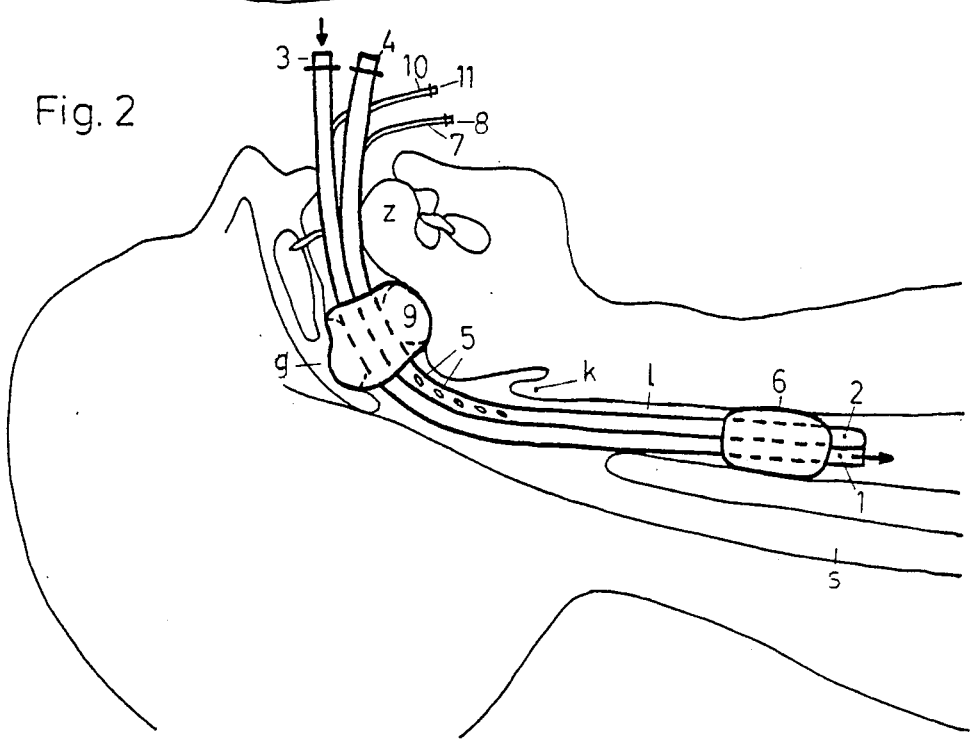

In the following the invention with its additional advantages and features is explained more in detail, by way of examples, being shown in the drawings. FIG. 1 shows a twin-lumen airway according to the invention, being inserted in the esophagus, in a schematic view, FIG. 2 shows the same airway being inserted in the trachea, FIG. 3 shows an airway according to the invention in a side elevation view, FIG. 4 shows a detail of a single-lumen airway according to the invention in a side elevation view, FIG. 5 shows a cross-section according to the line v—v in FIG. 4, FIG. 6 shows a look at the tip of a twin-lumen airway according to the invention in the direction of the airway-axis and FIG. 7 shows the tip in a side elevation view.

FIG. 1 shows a twin-lumen airway suitable for ventilation in endotracheal or esophageal-obturator position by choice. The airway has one continuous lumen 1 with an open distal end and a second lumen 2 which is sealed at the tip of the airway. The lumens 1 and 2, either in parallel or coaxial to one another, are conducted separately at the upper end of the airway and are provided with connectors 3 and 4. Further the airway has air-outlets 5 connected with one lumen 2.

In the area of its lower end the wall of the airway is surrounded by an inflatable cuff 6. Said cuff 6 is connected by means of a duct 7, shown only partially, to a connector 8. Furthermore the airway has an inflatable pharyngeal cuff 9 which, in the same way as the cuff 6, surrounds the wall of the airway and is connected to a connector 11 by means of a duct 10.

For esophageal obturator ventilation the airway is inserted in the esophagus as shown in FIG. 1 and a mark, not definitely shown in the figures at the upper end of the airway, shows its correct positioning. Then the cuff 6 is inflated by using the connector 8 and the duct 7. The cuff 6 extends to a length of approxiamately 4,5 cm and is positioned approximately 1,5 cm from the tip of the airway. When being inflated, the cuff blocks the esophagus.

The pharyngeal cuff 9 is inflated by using the connector 11 and the duct 10. As shown in the figures the pharyngeal cuff 9 is positioned on the airway above the air-outlets 5 in such a way that it is situated between the soft palate and the boundary between the base of the tongue and the back of the tongue when the airway is in an inserted position. In the drawings the tongue is marked with z. As the soft palate g is pushed in a dorsocranial direction, not only the connection between the cavum pharyngis and the cavum oris but also between the cavum pharyngis and the cavum nasi is blocked.

Air for ventilating the patient is forced through the connector 4 into the lumen 2 of the airway and then flows through the air-outlets into the trachea and vice versa. It can be recognized easily that the dead-volume for air already consumed is very small.

In the endotracheal position according to FIG. 2 the cuff 6 and the pharyngeal cuff 9 are inflated as already described. As in this case the ventilation is carried out by using the connector 3 and the lumen 1 it is not essentially necessary but advantageous to inflate the pharyngeal cuff 9, for it firmly keeps the airway in its correct position.

The recommended dimensions for an airway according to the invention are shown in FIG. 3 more in detail. The teeth of the patient are marked with t. The distance a from that point of the inserted airway, which lies between the teeth of the patient, to the pharyngeal cuff 9 is 9 to 12 cm, in most cases 10 cm. The pharyngeal cuff, thich is of toroid shape when being inflated, is fixed, e.g. glued, vulcanized, bound etc. to the wall of the airway along a distance b of 1.5 to 2.5 cm. The volume of the pharyngeal cuff, which is made of a flexible, maybe even elastic material, is 60 to 110 ml. In a distance c of approximately 8 cm from the center of the pharyngeal cuff 9 there is the upper (oral) end of the inflatable cuff 6. Said cuff 6 extends to a lenght d of approximately 4.5 cm and ends in a distance e of approximately 1.5 cm from the tip of the airway. The dimensions given above refer to an airway which is based on the anatomy of an average-sized adult. Measures of airways for children or babies have to be reduced appropriate.

The upper (oral) wall 12 of the pharyngeal cuff may be thinner than the caudal (lower) wall. In this way the pharyngeal cuff expands more in an oral direction, as shown in FIG. 3, dotted line if the pharyngeal cuff is filled to much. This avoids that the pharyngeal cuff tends to close the epiglottis k (FIG. 1).

FIGS. 4 and 5 shows an embodiment of the airway which avoids blocking of the air-outlets 5 by mucosa or other parts of the body. This blocking would made expiration impossible. For this purpose there are longitudinal bars 13 between the air-outlets 5, which keep e.g. the mucosa away from the air-outlets. These bars 13 may also have some other course, e.g. they may be S-shaped or may be interrupted in places. Instead of the bars there also may be naps or the like but the insertion of the airway should not be made more difficult and the danger of injuring the patient should not be enlarged.

In FIGS. 6 and 7 a cap 14 is shown which closes the tip of a twin-lumen airway. Both lumens have the same reference numerals 1 and 2 as in FIG. 1. The cap 14 shows the shape of a hollow hemisphere in general. In the cap there is a hole 15 opposite to the open lumen 1. The diameter of the hole is less in width than the diameter of the lumen 1. Furthermore there are additional holes 16 in the cap 14, whose diameter is also smaller than the diameter of the lumen 1 and also smaller than the diameter of the hole 15. The holes 16 may be ommited or an other number of holes may be provided.

At that end of the cap 14 which faces the airway in the area of the lumen 2 the cap has a base 17 with a protuberating plug 18. Corresponding to the diameter of the lumen 2 the diameter of the plug 18 is semicircular in the example. When attaching the cap 14 into the airway the plug is put into the end of lumen 2 which therefore is blocked. The cap 14 may be glued to the airway.

The holes 15 and 16 enable pass through of air or liquids but prevent bigger particles, e.g. residues of food, to get into the lumen 1 and to block it. As the hole 15 is opposite to the lumen 1, it is possible to insert catheters etc. without problems into the stomach or further into the intestines.

We claim:

1. An airway for both sole esophageal obturator ventilation and for combined endotracheal and esophageal obturator ventilation of a patient, selectively, comprising:

tube means having a proximal end, and a distal end, said distal end being insertable into an esophagus and into a trachea selectively, said tube defining two lumens extending axially thereof both of which are open at said proximal end, the distal end of one of said lumens being open and the distal end of the other of said lumens being closed, said tube means defining at least one air outlet communicating with said lumen having said closed distal end and which is locatable in a patient's pharyngeal area;

an inflatable distal cuff on said tube means located adjacent the distal end of said tube means;

distal inflation means connected between said inflatable distal cuff and said proximal end of said tube means for allowing selective inflation of said inflatable distal cuff;

an inflatable pharyngeal cuff on said tube means located between said at least one pair outlet and said proximal end of said tube means, said pharyngeal cuff having a toroidal shape being sized and located with respect to said tube means such that when inflated, it is situated within the boundaries of a pars oralis of a patient, and;

pharyngeal inflation means connected between said inflatable pharyngeal cuff and said proximal end of said tube for allowing selective inflation of said pharyngeal cuff.

2. An airway according to claim 1, characterized in that the volume of the filled pharyngeal cuff is from 60 to 110 ml.

3. An airway according to claim 1, characterized in that the pharyngeal cuff is placed in a position 9 to 12 cm from that part of the airway which is located between the teeth of the patient when the airway is inserted.

4. An airway according to claim 1, characterized in that the oral wall of the pharyngeal cuff is thinner than the caudal wall so that the cuff expands into the direction of the mouth when being filled to a higher extent.

5. An airway according to claim 1, characterized in that said tube means has protuberances in the area of the air-outlets.

6. An airway according to claim 5 wherein said protuberances extend radially to both circumferential sides of each said air outlet and along an axial length of said tube means to each longitudinal side of each said air outlet.

7. An airway according to claim 1 wherein:

said tube means further comprises:
a cap which is generally hemispheric and closes said closed lumen at the distal end of said tube means, said cap having an open lumen orifice of smaller area than the open area of said open lumen, said open lumen orifice being located on a portion of said cap surface which is approximately parallel to the axis of said open lumen, and said open lumen orifice being in fluid communication with said open lumen.

8. An airway according to claim 7, characterized in that the cap has additional open lumen orifices, their area being likewise smaller than the area of said open lumen, and said additional orifices being in fluid communication with said open lumen.

9. An airway according to claim 7, characterized in that the cap has a plug which blocks said closed lumen.

* * * * *

UNITED STATES PATENT AND TRADEMARK OFFICE
CERTIFICATE OF CORRECTION

PATENT NO. : 4,688,568

DATED : August 25, 1987

INVENTOR(S) : Michael Frass et al

It is certified that error appears in the above-identified patent and that said Letters Patent is hereby corrected as shown below:

Column 4, line 38, "pair" should have been --air--.

Signed and Sealed this

Twenty-second Day of March, 1988

Attest:

DONALD J. QUIGG

Attesting Officer

Commissioner of Patents and Trademarks